United States Patent [19]

McKelvy

[11] 4,097,113
[45] Jun. 27, 1978

[54] ELECTRICAL CONNECTORS FOR PORTABLE ELECTRONIC PHYSIOLOGICAL INSTRUMENTS HAVING SEPARABLE FIRST AND SECOND COMPONENTS

[75] Inventor: Stephen L. McKelvy, Woodinville, Wash.

[73] Assignee: Physio-Control Corporation, Redmond, Wash.

[21] Appl. No.: 720,148

[22] Filed: Sep. 3, 1976

[51] Int. Cl.² .................................................. A61N 1/36
[52] U.S. Cl. .......................... 339/256 R; 128/2.06 G; 128/419 D
[58] Field of Search ................ 339/256 R, 65, 198 H, 339/198 GA, 198 J, 125 R, 150 T; 128/2.05 R, 2.06 A, 2.06 G, 2.06 R, 419 D, 419 P, 419 R

[56] References Cited

U.S. PATENT DOCUMENTS

| 819,060 | 5/1906 | Guttman | 339/198 H X |
|---|---|---|---|
| 3,764,955 | 10/1973 | Ward | 339/65 |
| 3,968,323 | 7/1976 | Blanchet | 339/198 GA X |

Primary Examiner—William E. Kamm

Attorney, Agent, or Firm—Christensen, O'Connor, Johnson & Kindness

[57] ABSTRACT

An EKG monitor/recorder and defibrillator which are contained in separate housings are mechanically interconnected by a tongue member located on an exterior surface of the housing of the EKG monitor/recorder and a groove member located on an exterior surface of the housing of the defibrillator. The groove member receives the tongue member with a translative, sliding fit to also permit easy disconnection and separation of the EKG monitor/recorder and the defibrillator. Electrical interconnection between the EKG monitor/recorder and the defibrillator is afforded by a pair of novel electrical slide connectors respectively located in the exterior surfaces of the housings in proximity to the tongue and groove members, with each electrical slide connector including a plurality of spaced-apart leaf spring contacts which, in assembly, extend parallel to the direction of translative movement of the EKG monitor/recorder and defibrillator housings. Circuitry is provided within the EKG monitor/recorder and defibrillator for providing EKG monitoring through paddle electrodes of the defibrillator by coupling the paddle electrodes to the EKG monitor/recorder through the pair of electrical slide connectors.

4 Claims, 11 Drawing Figures

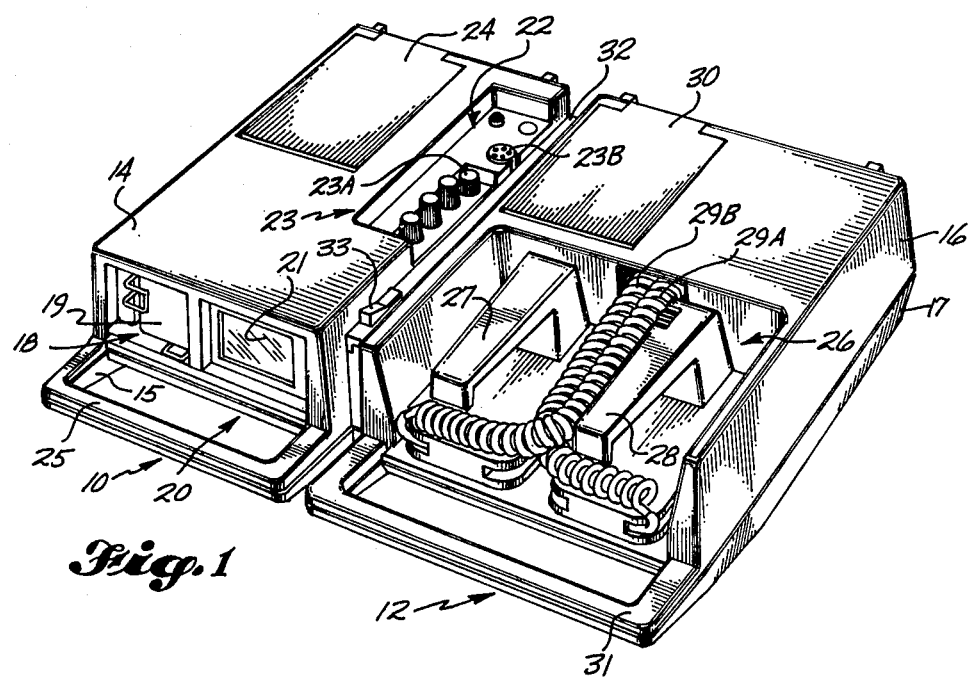

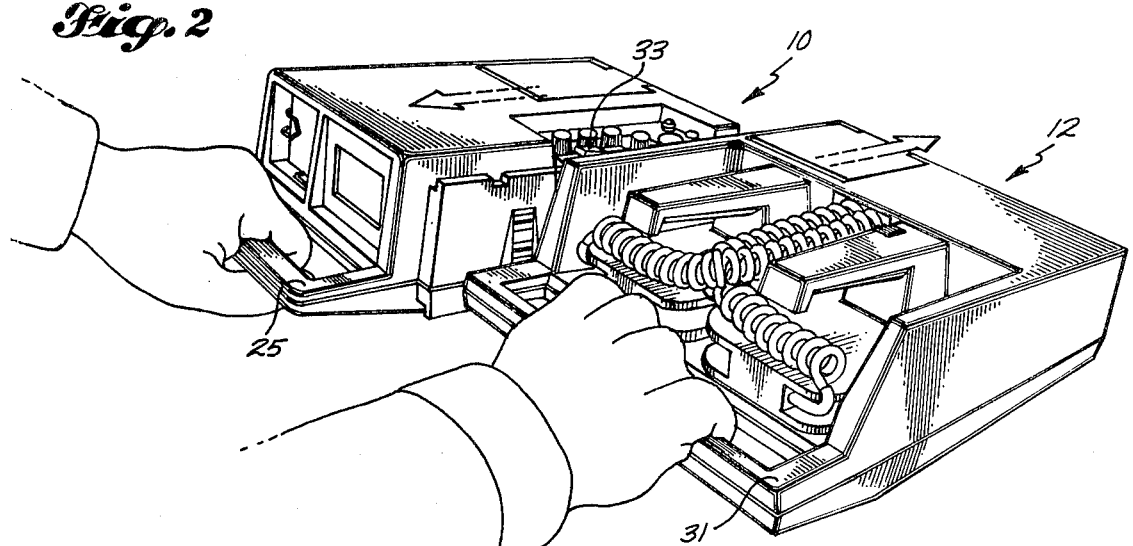
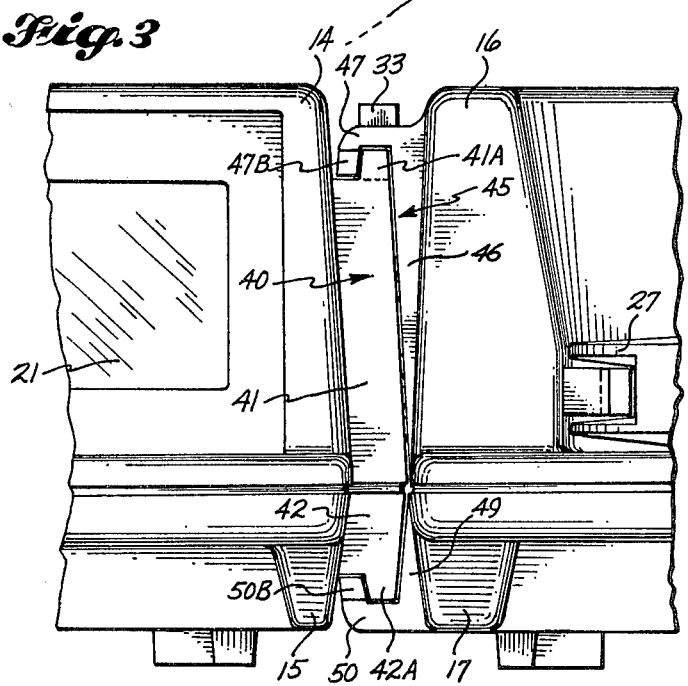
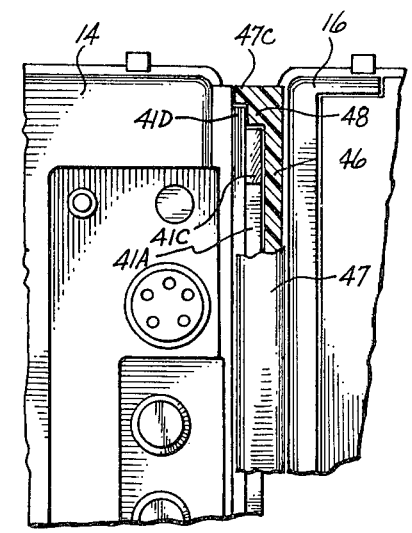
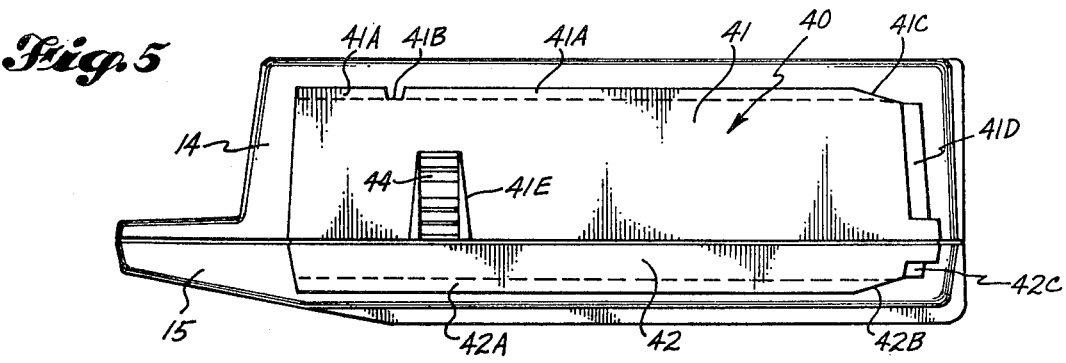

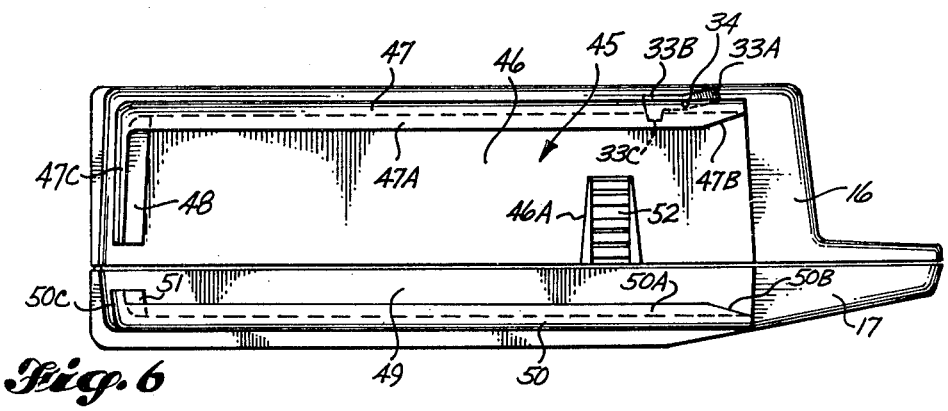
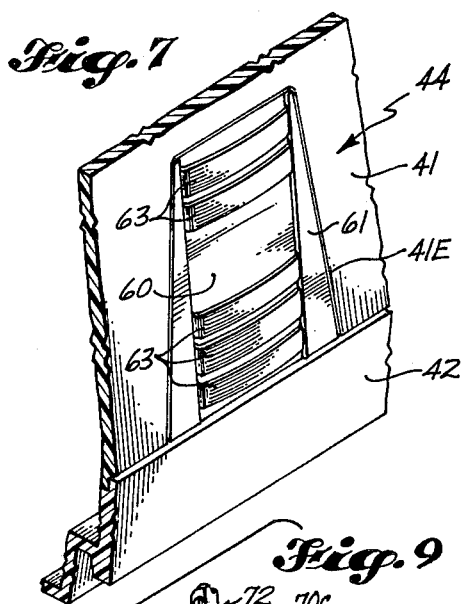
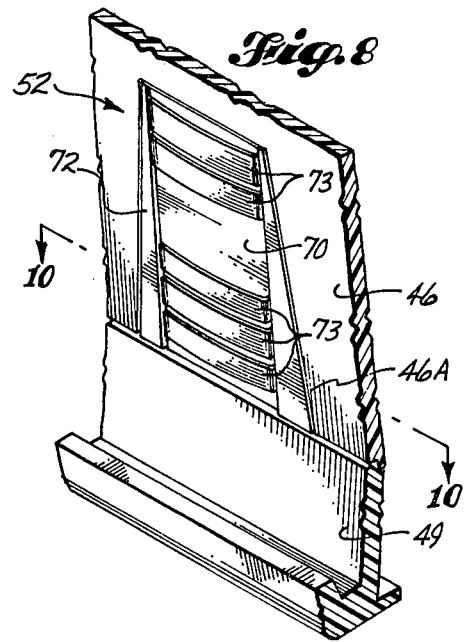
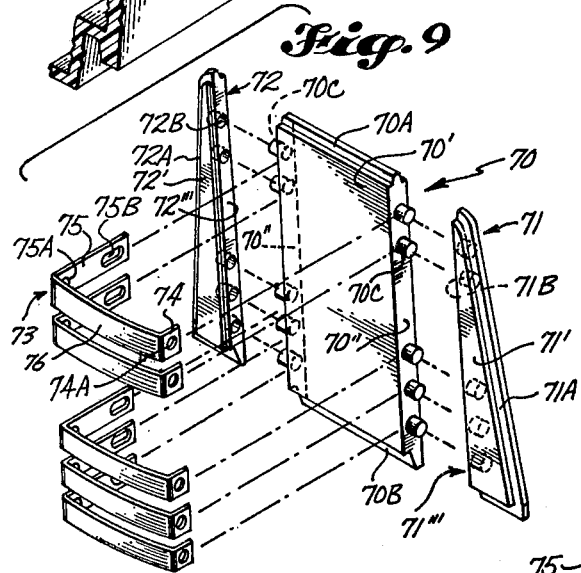
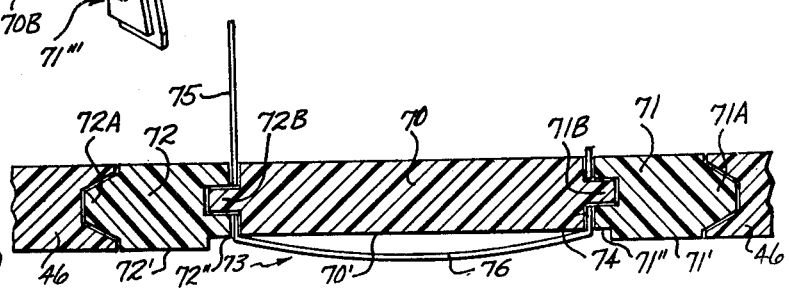

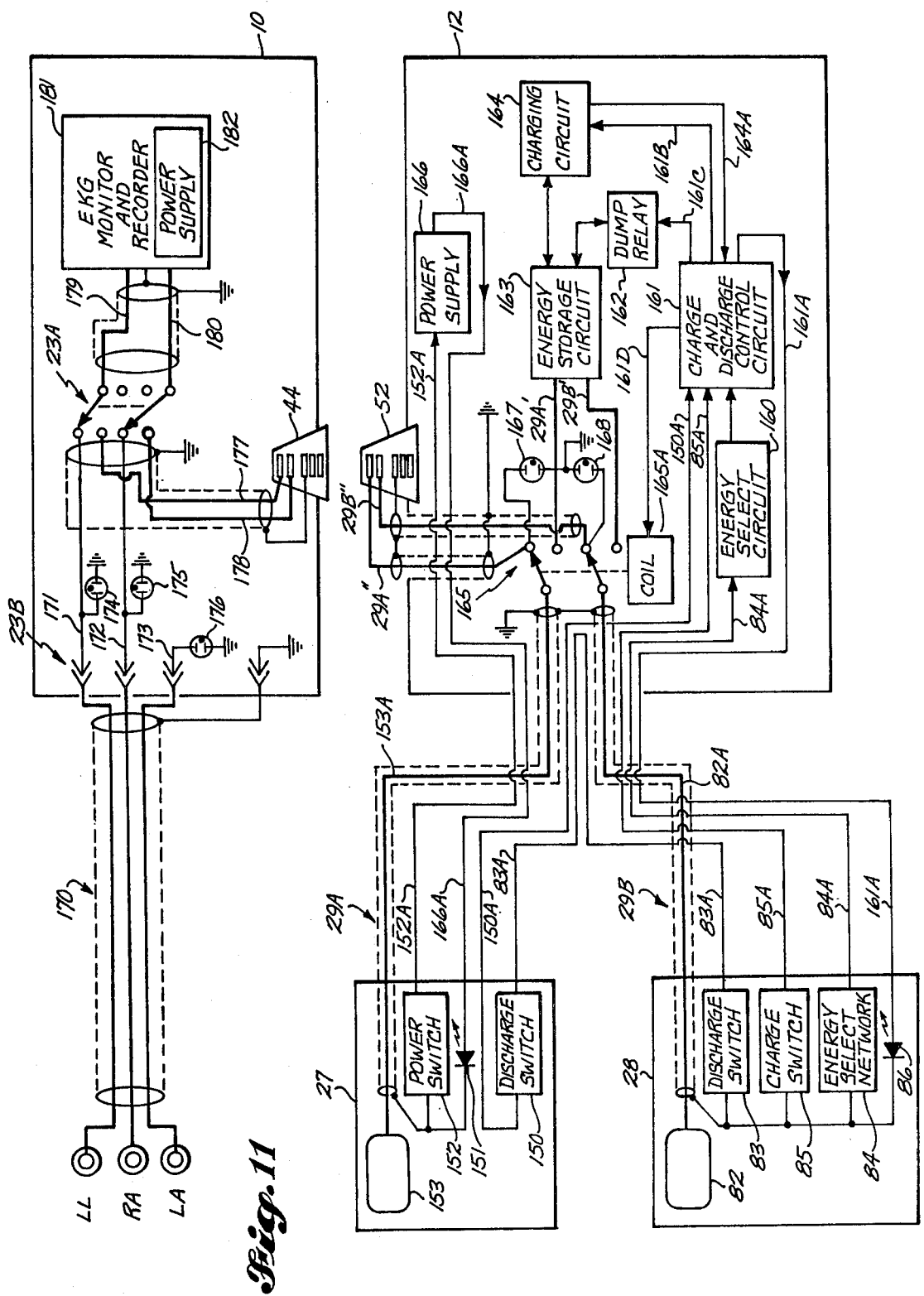

ELECTRICAL CONNECTORS FOR PORTABLE ELECTRONIC PHYSIOLOGICAL INSTRUMENTS HAVING SEPARABLE FIRST AND SECOND COMPONENTS

FIELD OF THE INVENTION

This invention generally relates to electrical connectors, and more particularly, to electrical connectors for portable electronic physiological instruments having a first component, such as an EKG monitor, and a second component, such as a defibrillator, which are separable for stand-alone use.

BACKGROUND OF THE INVENTION

Electronic physiological instruments are well known to the prior art and include such products as electrocardiographic (EKG) monitors, EKG recorders, and defibrillators.

EKG monitors typically provide for real-time or non-real-time display of a patient's EKG waveform and are typically interconnected with the patient via a set of electrodes and associated conductors commonly referred to as a patient cable. Similarly, an EKG recorder provides for permanent recording of the patient's EKG waveform over a period of time, utilizing, for example, a strip-chart recorder, and is also typically connected to the patient via a patient cable. Accordingly, both EKG monitors and EKG recorders are diagnostic instruments, that is, they assist the user in evaluating the physiological condition, and in particular, the cardiac condition of the patient.

On the other hand, a defibrillator is a therapeutic instrument particularly useful in conjunction with EKG monitors and EKG recorders to assist in curing certain cardiac irregularities, notably those of ventricular and atrial fibrillation. The defibrillator is typically interconnected with the patient via a set of large paddle electrodes and associated conductors and operates to apply a high-energy DC pulse or pulses to the patient via the associated conductor and paddle electrodes when appropriately triggered by the user.

It is known in the prior art to combine two or more of these electronic physiological instruments within a single housing and to provide internal electrical interconnection therebetween. Reference should be made to U.S. Pat. No. 3,547,108, Seiffert, et al., which is assigned to the assignee of the present invention, for an illustration of such prior art. In U.S. Pat. No. 3,547,108, circuitry is provided to allow an EKG monitor to be connected to the patient through the paddle electrodes and associated conductors normally used for the defibrillator, and to be disconnected therefrom when a defibrillation pulse is to be applied.

It is also known in the prior art to make such combination instruments portable and self-contained, e.g., with an internal battery or power source. Such portable combination instruments have proved to be extremely useful in treating cardiac emergencies and have led to the establishment throughout the world of mobile, paramedic-staffed emergency rescue units equipped with such instruments, which emergency rescue units have saved many lives due to the quickness with which they can respond to, diagnose, and treat a person with cardiac abnormalities.

Those skilled in the art will readily appreciate that, in order to be useful to such mobile emergency rescue units, combination electronic physiological instruments must include a number of features. First, they should be simple to operate. Second, they should be portable, that is, their weight should be as low as possible, and their size should be as small as possible. Third, they must be both electrically and mechanically reliable and should be particularly rugged to withstand adverse environment considerations.

While most combination instruments typically known to the prior art exhibit these features to a greater or lesser degree, there is one particular circumstance in which they do not. It is often desirable to have the component instruments of the combination both mechanically and electrically separable. In many practical situations, it is necessary to have only a portable defibrillator, or only a portable EKG monitor and/or EKG recorder available and usable as a stand-alone instrument. For example, when an emergency rescue unit transports a patient to a hospital in an ambulance or other vehicle after some cardiac stability has been achieved by use of a defibrillator, only monitoring and recording of the patient's EKG waveform is needed. In such instances, a defibrillator is unneeded.

In the prior art, this problem of separability may be attacked by utilizing separate portable electronic physiological instruments contained in separate housings which are interconnected by cables, in which case the weight, size and simplicity of operation advantages of combination instruments are lost.

A more recent approach in the prior art is to provide a combination instrument in which an EKG monitor is located in a housing which can be received in a receptacle located within a larger housing in which a defibrillator is located. Respective electrical connectors are located within the defibrillator receptacle and on a corresponding portion of the monitor housing and are interengaged when the monitor housing is inserted into the defibrillator receptacle to provide the electrical interconnection necessary to afford a monitoring through the paddles feature, such as disclosed in the aforementioned U.S. Pat. No. 3,547,108, as well as to provide charging current to a rechargable battery located within the monitor housing. Since the EKG monitor is provided with its own patient cable, or with a connector for attaching a patient cable thereto, and since it has a rechargable battery, it can be removed from the defibrillator housing and used as a stand-alone item.

However, such apparatus has proved to be disadvantageous in many respects. For example, when the monitor housing is removed from the defibrillator housing, the open receptacle within the defibrillator housing accumulates foreign matter, such as debris, liquid, and so forth which must be removed from the receptacle before the monitor housing is re-inserted. In many cases, the contacts in the electrical connectors within the defibrillator receptacle and on the monitor housing can become fouled by such foreign matter accumulation or upon re-insertion of the monitor housing, leading to damage or improper operation of the defibrillator or the monitor. Further, the provision of a rechargable battery within the monitor housing and charging circuitry for that rechargable battery within the defibrillator housing requires that the monitor be re-inserted in the defibrillator housing at periodic intervals, thus limiting the usefulness of the monitor as a stand-alone item.

It is therefore an object of this invention to provide a novel electrical connector which affords greatly reduced susceptability to failure or improper operation of an associated electronic physiological instrument due to fouling of the connector contacts.

It is a further object of this invention to provide novel electrical connectors which are particularly useful when installed in pairs in complementary walls of separable first and second components of an electronic physiological instrument.

SUMMARY OF THE INVENTION

Briefly, these objects and others which will be recognized by those skilled in the art are achieved by an improved electrical connector for electronic physiological instruments, the connector comprising a central contact support member of insulating material which has a substantially rectangular, substantially planar front surface and a pair of opposite, substantially parallel side surfaces bounding the front surface. First and second contact retaining members, each of insulating material, are also provided, each having a substantially planar front surface and an adjoining side surface complementary to one of the pair of side surfaces of the central contact support member. A plurality of metallic, leaf spring contacts are provided, with each contact being formed into a substantially U-shape and thereby having a central, bowed contact portion, and adjoining first and second legs, each of the legs having extending therethrough an aperture, and electrical terminal means being provided on one of the legs. A plurality of projections are formed and extending from the side surfaces of one of the central contact support member or the first and second contact retaining members, the plurality of projections being spaced from each other. A corresponding plurality of recesses are formed in the side surfaces of the other of the central contact support member or the first and second contact retaining members, the plurality of recesses being spaced apart from each other. The first and the second contact retaining members are secured to the central contact support member with each one of a plurality of projections passing through one of the apertures in a leg of one of a plurality of contacts and being received in a corresponding one of the plurality of recesses.

BRIEF DESCRIPTION OF THE DRAWINGS

The invention can perhaps best be understood by reference to the following portion of the specification, taken in conjunction with the accompanying drawings in which:

FIG. 1 is a pictorial view of a portable electronic physiological instrument including a first component comprising an EKG monitor/recorder and a second component comprising a defibrillator;

FIG. 2 is a pictorial view illustrating the EKG monitor/recorder and defibrillator of the portable electronic physiological instrument illustrated in FIG. 1 in the act of separation thereof;

FIG. 3 is a front elevation view illustrating a portion of the arrangement for mechanically interconnecting the EKG monitor/recorder and defibrillator of the instrument of FIG. 1;

FIG. 4 is a partial cutaway top view of a portion of the arrangement of FIG. 3;

FIG. 5 is a side elevation view of the EKG monitor/recorder illustrating further details of the mechanical arrangement and also illustrating the novel electrical connector of the present invention;

FIG. 6 is a side elevation view of the defibrillator illustrating further details of this mechanical arrangement and also illustrating the novel electrical connector;

FIG. 7 is a partial pictorial view of the novel electrical connector as installed in the EKG monitor/recorder;

FIG. 8 is a partial pictorial view of the novel electrical connector as installed in the defibrillator;

FIG. 9 is an exploded pictorial view of the novel electrical connector;

FIG. 10 is a sectional view of the novel electrical connector as installed in the defibrillator and as taken along the lines 10—10 in FIG. 8; and FIG. 11 is a combined schematic and block electrical diagram of the portable electronic physiological instrument.

DESCRIPTION OF A PREFERRED EMBODIMENT

Referring now to FIG. 1, the portable electronic physiological instrument illustrated therein includes a first component comprising a portable EKG monitor/recorder and generally designated by the reference numeral 10, and a second component comprising a portable defibrillator and generally designated by the reference numeral 12.

The monitor/recorder 10 is contained in a housing consisting of an upper housing 14 and a lower housing 15 which are joined and sealed together. Likewise, the defibrillator 12 is contained in a housing consisting of an upper housing 16 and a lower housing 17 which are joined and sealed together. Preferably, housings 14, 15, 16 and 17 are formed by injection molding a suitable insulating plastic material, such as phenylene oxide. A first opening 18 is provided in a front surface of the upper housing 14 for permitting access to a conventional EKG strip-chart recorder 19 forming part of the monitor/recorder 10 and located within its housing, and a second opening 20 is provided adjacent to the first opening 18 for permitting viewing of a conventional EKG monitor display 21 forming part of the monitor/recorder 10 and also located within its housing. A plurality of operating controls and connectors 23 for the monitor/recorder 10 are mounted in the upper housing 14 and located within a recess 22 in the upper right side thereof. The controls and connectors 23 include a patient cable-paddle switch 23A and a patient cable connector 23B. Electrical power for the monitor/recorder 10 is afforded by a rechargable battery pack 24 received in a corresponding recess, not illustrated, in upper housing 14. The battery pack 24 may be removed from the monitor/recorder 10 and placed in a separate charging apparatus, not illustrated, for recharging the batteries therein, while continued operation of the monitor/recorder is assured by inserting another battery pack 24. Both the upper housing 14 and the lower housing 15 have a substantially U-shaped extension in the front thereof to define in combination a handle 25 for the monitor/recorder 10.

A recess 26 is provided at the upper front of upper housing 16 of the defibrillator 12 for receiving and retaining a pair of removable defibrillator paddles, these being a sternum paddle 27 and an apex paddle 28. The paddles 27 and 28 are somewhat similar to those of the prior art and include an upper, insulating member having a handle which is to be grasped by the user, and a lower, metallic plate electrode which is to be placed in contact with the patient (with electrical conductance between the patient and plate electrodes being improved by the use of a conductive jelly or paste as in conventional). The sternum paddle 27 and the apex paddle 28 are respectively connected to the defibrillator 12 by coiled cables 29A and 29B. Included in the cables 29A and 29B are conductors interconnecting the metallic plate electrodes in paddles 27 and 28 with the portions of defibrillator 12 located within the defibrillator housing. Also included in the upper, insulating members of the paddles 27 and 28, but not illustrated, are a plurality of operating controls and indicators for the defibrillator 12, with electrical connections between these operating controls and indicators and the portions of defibrillator 12 located within the defibrillator housing being made by corresponding conductors in the coiled cables 29A and 29B. Reference will be made hereinafter to a detailed description of the electrical structure and function of these operating controls in conjunction with the remaining portions of defibrillator 12 as illustrated in the combined schematic and block electronic diagram of FIG. 11.

As with the monitor/recorder 10, the defibrillator 12 includes a battery pack 30 received in a corresponding recess, not illustrated, in the upper housing 16 for supplying electrical power to the defibrillator 12. The battery pack 30 may be identical in construction to the battery pack 24 and interchangable therewith. In this manner, the battery pack 30 may be removed from the defibrillator 12 and inserted into the monitor/recorder 10 in place of battery pack 24 in a situation where the battery pack 24 requires recharging, and vice-versa, thus providing increased operation time for either the monitor/recorder 10 or the defibrillator 12 when used as a stand-alone item.

As with the monitor/recorder 10, defibrillator 12 has a handle 31 defined by first and second protruding, substantially U-shaped extensions of upper housing 16 and lower housing 17.

As illustrated in FIG. 1, the monitor/recorder 10 and defibrillator 12 are mechanically and electrically interconnected through an arrangement generally indicated at 32 and controlled by a rotatable latch 33, all as detailed in FIGS. 3–10.

The separation of monitor/recorder 10 and defibrillator 12 into separate components is carried out as illustrated in FIG. 2, wherein the user has previously depressed rotatable latch 33 and is in the process of effecting the separation by pushing on handle 31 of defibrillator 12 while simultaneously pulling on handle 25 of monitor/recorder 10. It will be seen that monitor/recorder 10 and defibrillator 12 separate after depression of rotatable latch 33 by simple and opposing translative movements thereof in the directions of the arrows in FIG. 2.

Referring now to FIGS. 3–8, the mechanical interconnection of the arrangement generally indicated at 32 in FIG. 1 is afforded by a tongue member 40, forming part of the housing of the monitor/recorder 10, and a groove member 45, forming part of the housing of defibrillator 12, for receiving the tongue member 40.

The tongue member 40 is divided into a first member 41 forming part of and extending from the right-side surface of the upper housing 14 and a second member 42 forming part of and extending from the right-side surface of the lower housing 15, with the members 41 and 42 extending for substantially the entire length and height of the right-side surface of the monitor/recorder 10, as best illustrated in FIG. 5. The first member 41 defines a first tongue 41A its upper extremity and the second member 42 likewise defines a second tongue 42A at its lower extremity, with tongues 41A and 42A extending lengthwise with respect to the right-side surface of the monitor/recorder 10. A notch 41B is provided in the tongue 41A near the front of monitor/recorder 10 for receiving a portion of the rotatable latch 33 to be hereinafter described. The upper surface of the tongue 41A terminates in a downwardly-sloping cam surface 41C located adjacent the rear of monitor/recorder 10. Likewise, the lower surface of the tongue 42A terminates in an upwardly-sloping surface 42B located adjacent the rear of monitor/recorder 10. A first locking member 41D is formed as part of the upper housing 14 adjacent the rearward termination of the first member 41 and a second locking member 42C is formed as part of the lower housing 15 adjacent the rearward termination of the second member 42. The first member 41 (and corresponding underlying portions of the upper housing 14) is cut away at 41E to receive a first slide connector 44 to be hereinafter described.

The groove member 45 is divided into a first member 46 forming part of and extending from the left-side surface of the upper housing 16 and a second member 49 forming part of and extending from the left-side surface of the lower housing 17. As best seen in FIG. 6, the members 46 and 49 extend for substantially the entire length and height of the left-side surface of the defibrillator 12. Extending from and forming a part of the first member 46 at its upper extremity is a first hook-like member 47. A second hook-like member 50 likewise extends from and forms part of the second member 49 at its lower extremity.

The first hook-like member 47 is seen to have a dependent arm 47A which defines, in conjunction with first member 46, a groove for receiving the first tongue 41A of the tongue member 40. Likewise, the second hook-like member 50 is seen to have an upstanding arm 50A, which, in conjunction with second member 49, defines a groove for receiving the second tongue 42A. A lower surface of the dependent arm 47A is inclined at 47B, as is an upper surface of the upstanding arm 50A at 50B, at locations adjacent the front of defibrillator 12 to facilitate insertion of the tongues 41A and 42A into their corresponding grooves.

At the rear of defibrillator 12, the first hook-like member 47 changes direction by substantially 90° to form a substantially vertically-extending stop member 47C. Likewise, the hook-like member 50 changes direction by substantially 90° to form a substantially vertically extending stop member 50C. Located adjacent stop members 47C and 50C respectively, are locking members 48, 51 formed as parts of and extending from the upper housing 16 and lower housing 17, respectively.

The rotatable latch 33 is mounted in a corresponding aperture, not illustrated, in first hook-like member 47 near the front of defibrillator 12 and is supported for rotation therein by a pin 34 itself rigidly supported in corresponding apertures in hook-like member 47. Rotatable latch 33 includes a first lever arm 33A which extends above the top of first hook-like member 47 is assembly and a second, opposite lever arm 33B contained within the aperture in hook-like member 47 having at its end a downwardly dependent projection 33C configured to engage the notch 41B in tongue 41A.

The first member 46 (and corresponding underlying portions of the upper housing 16) is cut away at 46A to receive a second slide connector 52 to be hereinafter described.

As can best be seen in FIG. 3, the members 41 and 46, and 42 and 49, are complementary in configuration and lie in close proximity to each other when the tongue 41A is inserted into the groove afforded by hook-like member 47 and the tongue 42A is inserted into the groove afforded by hook-like member 50. Additionally, it will be noted that the arms 47B and 50B of hook-like member 47 and 50 are received in respective grooves defined by the tongue 41A and a corresponding side surface of upper housing 14, and the tongue 42A and a corresponding side surface of lower housing 15. As a result, the mechanical interconnection afforded thereby is both rugged and substantially free from movement in directions parallel to the height and width of the monitor/recorder 10 and defibrillator 12.

Substantial freedom of movement of the mechanical interconnection in a direction parallel to the length of the monitor/recorder 10 and defibrillator 12 is afforded in the following manner.

When the tongue member 40 is inserted into the groove member 45 and thereafter the monitor/recorder 10 and defibrillator 12 are moved in directions opposite to that illustrated in FIG. 2, the cam surface 41C first comes into contact with the projection 33C on rotatable latch 33. Further translative movement results in latch 33 being rotated upwardly through the second lever arm 33B. The monitor/recorder 10 and defibrillator 12 are then continued to be moved in opposite directions. This lengthwise, translative movement is terminated when stop member 47C abuts the rearward surface of the locking member 41D, as best illustrated in FIG. 4, and stop member 50C abuts the rearward surface of the locking member 41D, as best illustrated in FIG. 4, and stop member 50C abuts the rearward surface of locking member 42C. Just before this point is reached, it will be noted that locking member 41D has come into contact with corresponding locking member 48, also as illustrated in FIG. 4. As best seen in FIG. 3, a slight separation is afforded between the complementary members 41, 46 and 42, 49 when in assembly to allow friction-free translation thereof. However, complementary locking members 41D and 48 are configured in assembly to frictionally engage during the aforementioned relative movement of monitor/recorder 10 and defibrillator 12, thereby affording a positive restriction against further movement which can be overcome only by the user exerting additional force on the handles 25 and 31. A corresponding frictional engagement also occurs between the complementary locking members 42C and 51.

When the monitor/recorder 10 and defibrillator 12 are in the position illustrated in FIGS. 1, 3 and 4, the projection 33C of rotatable latch 33 is aligned with the notch 41D and drops thereinto by the force provided by a torsional spring, not illustrated, thereby providing a complete restraint against longitudinal movement.

The aforementioned apparatus for mechanically interconnecting the monitor/recorder 10 and defibrillator 12 forms no part of the present invention and is claimed in a copending patent application entitled "Portable Electronic Physiological Instrument Having Separable First and Second Components, and Improved Mechanical Connector Therefor," by Smith et al., and assigned to the assignee of the present invention.

The cutaway portions 41E, 46A of upper housing 14, 16 are located so that when monitor/recorder 10 and defibrillator 12 are in their locked, assembled positions, electrical contacts of slide connectors 44 and 52 abut each other to provide electrical interconnection between the monitor/recorder 10 and the defibrillator 12.

Now referring to FIGS. 7–10, slide connector 44 includes a substantially rectangular, central contact support member 60 of insulating material upon which are supported a plurality of metallic, leaf spring contacts 63, each having its longitudinal dimension extending in a direction parallel to the longitudinal dimension of monitor/recorder 10 (and accordingly parallel to the direction of translative movement thereof when being moved in and out of assembly with defibrillator 12). In FIG. 7, the contacts 63 are illustrated as being spaced apart in a vertical direction along the central contact support member 60. First and second, substantially triangular contact retaining members 61, 62 of insulating material are also provided for retaining the plurality of contacts 63 in the connector and, together with central contact support member 60, for retaining the connector 44 within the housing of the monitor/recorder 10.

Likewise, with reference to FIG. 8, the slide connector 52 includes a central contact support member 70 of insulating material, a plurality of metallic leaf spring contacts 73, and first and second contact retaining members 71, 72 of insulating material. It should be noted (reference FIGS. 3, 7 and 8) that the junctures between upper housings 14, 16 and lower housings 15, 17 are aligned when the monitor/recorder 10 and defibrillator 12 are in assembly. Since the slide connector 52 is identical to slide connector 44 (and in fact may be assembled from the same component parts), and since slide connectors 44, 52 are respectively located in the complementary members 41, 46, the contacts 63, 73 thereof engage each other with a longitudinal wiping action when the monitor/recorder 10 and defibrillator 12 are moved relative to each other in assembly. Such a wiping action proves very effective in removing any contaminants that may accumulate on either or both of the slide connectors 44, 52 when the associated monitor/recorder 10 and defibrillator 12 are separated and used as stand-alone items.

The detailed construction of the slide connector 52, and its assembly with the housing of defibrillator 12, are illustrated in FIGS. 9 and 10.

The central contact support member 70 has a substantially rectangular, substantially planar front surface 70'. A plurality of substantially cylindrical, equi-diameter pins 70C (corresponding in number to the number of contacts 73) are provided on opposing, parallel side surfaces 70" of central contact support member 70 which bound front surface 70'. The pins 70C are located along surfaces 70" with a spacing corresponding to the desired vertical spacing of the contacts 73. Each of the contacts 73 is formed into a substantially U-shape including a first leg 74 having an aperture 74A therethrough, a bowed, central portion 76, and a second leg 75 having an aperture 75A and a conductor-receiving aperture 75B therethrough.

The contact retaining members 71, 72 have, respectively, substantially triangular, substantially planar front surfaces 71', 72', with respective edge portions 71", 72" that are indented with respect to the planes of surfaces 71', 72' (FIG. 10). In side surfaces 71''', 72''' adjoining edge portions 71", 72" there are located a plurality of recesses 71B, 72B, each of whose diameter approximates that of the apertures 74A, 75A in contacts 73 and the pins 70C on central contact support member 70. The vertical spacing of the recesses 71B,72B corresponds to that of pins 70C and accordingly with that of the desired vertical spacing of the contacts 73.

In assembly, the pins 70C are received through corresponding apertures 74A, 75A in contacts 73 and in the recesses 71B,72B. The contact retaining members 71,72 are secured to the central contact support member 70 by ultrasonic welding.

Assembled slide connector 52 is then inserted into the cutaway portion 46A. The central contact support member includes an upper peripheral tongue 70A and a lower peripheral tongue 70B, and the contact retaining members 71, 72 likewise have respective peripheral tongues 71A,72A. As best illustrated in FIGS. 8 and 10, the peripheral tongues 71A, 70A, 72A are received in corresponding grooves in the upper housing 16. Typically, a high temperature grease is used to seal the slide connector 52 within the upper housing 16. The lower portions of the tongues 71A, 72A and the tongue 70B then engage a corresponding groove in the lower housing 17 when lower housing 17 is joined to upper housing 16 to complete the assembly. Before assembly, electrical connections are made to the contacts 73 by passing conductors through the terminal apertures 75B and securing the conductors by soldering or otherwise.

In assembly, the front surfaces 71',72' are flush with the exterior surface of member 46, and the edge portions 71",72" are flush with the front surface 70', thereby defining a recess for the contacts 73. In this manner, only part of the central bowed portion of each contact 73 protrudes beyond the exterior surface of member 46 to further protect the contacts 73 from damage or fouling.

It will thus be apparent to those skilled in the art that the slide connectors 44, 52 are simple in construction, light in weight, and yet rugged in assembly to provide reliable electrical interconnection between the monitor/recorder 10 and the defibrillator 12 when required.

With reference now to FIG. 11, the monitor/recorder 10 has connected thereto a three-lead, shielded patient cable 170 through patient cable connector 23B. Defibrillator 12 has connected thereto the paddles 27,28 through respective coiled cables 29A, 29B. As previously described, the monitor/recorder 10 and defibrillator 12 are electrically interconnected via slide connectors 44 and 52.

The paddles 27, 28 each include therein, as previously described, a metallic plate electrode, and a plurality of operator controls and indicators for the defibrillator 12. Specifically, the sternum paddle 27 includes a paddle electrode 153, a discharge switch 150, a power indicator 151, and a power switch 152. Switch 150, indicator 151 and switch 152 may be conveniently located in the upper insulating member of the paddle 27 so as to be available for manipulation and viewing by the instrument user. Switches 150, 152 may comprise normally-open, momentary, close push button switches, whereas indicator 151 may comprise a light emitting diode.

Likewise apex paddle 28 includes a paddle electrode 82, a discharge switch 83, a charge switch 85, an energy select network 84, and a charge indicator 86. Again, switches 83,85, network 84 and indicator 86 may be located in the upper insulating member of the paddle 28 so as to be available for manipulation and viewing by the instrument user. Switches 83,85 may comprise normally open, momentary-close push button switches and indicator 86 may comprise a light emitting diode. Energy select network 84 may include, on the other hand, a resistive network with a rotatable wiper arm controllable by the instrument user to one of a predetermined number of positions to select a specific resistance value between the input and output of energy select network 84, and, accordingly, a pre-selected energy value for the defibrillation pulse to be applied.

The operation controls and indicators within paddles 27,28, as well as the plate electrodes 153,82 therein, are interconnected with the defibrillator 12 through their respective coiled cables 29A,29B. Specifically, plate electrode 153 is interconnected with a first movable contact of a transfer relay 165 via a conductor 153A contained in cable 29A, and plate electrode 82 is connected with a second movable contact of transfer relay 165 via a conductor 82A in cable 29B. Because of their use in transmitting the low level EKG waveform to the monitor/recorder 10, both conductors 153A and 82A are shielded for substantially their entire length as indicated in FIG. 11, with the shields being connected to common potential at the defibrillator 12.

One terminal each of power switch 152 and indicator 151 are connected in common to the shielding of conductor 153A. A second terminal of power switch 152 is connected via a conductor 152A running partially in cable 29A to an input of a power supply 166 which is connected by a lead 166A in cable 29A to a second terminal of the indicator 151. Momentary actuation of the power switch 152 toggles on the power supply 166 which supplies a signal on lead to indicator 151 to indicate a power "on" condition. A subsequent actuation of power switch 152 toggles off power supply 166 which at the same time removes the signal from lead 166A. A source of power for the power supply is provided by battery pack 30.

One terminal each of discharge switch 83, charge switch 85, energy select network 84, and indicator 86 is likewise connected in common to the shield for conductor 82A. The second terminal of charge switch 85 is connected via a conductor 85A running partially in cable 29B to a charge and discharge control circuit 161 which has a first output connected by a lead 161A in cable 29B to a second terminal of indicator 186. A second terminal of discharge switch 83 is connected with a first terminal of discharge switch 150 by a conductor 83 running partially in cable 29B, through defibrillator 12, and partially in cable 29A. A second terminal of discharge switch 150 is connected to charge and discharge control circuit 161 via a conductor 150A running partially in cable 29A.

Charge and discharge control circuit 161 has a second output which is connected by a lead 161B to a charging circuit 164, a third output connected by a lead 161C to a dump relay 162, and a fourth output connected by a lead 161D to a coil 165A of the transfer relay 165. Both dump relay 162 and charging circuit 164 are interconnected in turn with an energy storage circuit 163 which has two output leads 29A',29B', connected to respective first and second stationary contacts of transfer relay 165. Charging circuit 164 also has an output connected by a lead 164A to charge and discharge control circuit 161.

In operation of the defibrillator 12 as a stand-alone item, the instrument user selects one of the predetermined energy levels by manipulation of energy select network 82 so that a representative signal is supplied to charge and discharge control circuit 161 by energy select circuit 160. Then, the user momentarily depresses charge switch 85 to provide a signal to set charge and discharge control circuit 161 via conductor 85A. A charging signal is thereafter applied by charging circuit 164 to energy storage circuit 163 to charge a capacitor within the preselected level. Typically, energy storage circuit 163 may include this capacitor and a wave-shaping inductor in series, as is conventional, with charging circuit 164 comprising an inverter supplying a high frequency charging waveform across the capacitor. A signal representative of the actual energy level to which the capacitor has been charged is supplied by charging circuit 164 on lead 164A to a comparator within charge and discharge control circuit 161, which comparator is also provided with a signal representative of the selected energy level obtained from energy select circuit 160. When the signals to this comparator equal each other, charge and discharge control circuit 161 removes the output signal from lead 161B to terminate the charging process.

During the charging process, or, during the time that an output signal is provided on lead 161B, charge and discharge control circuit 161 provides a pulsed output signal on lead 161A to cause indicator 86 to flash. When the charging process is complete, the signal on lead 161A changes to a steady-state signal, signifying to the user thorough indicator 86 that the defibrillator 12 is ready for discharge.

To discharge the defibrillator 12, the user must concurrently depress series-connected discharge switches 83 and 150, thereby completing a circuit therethrough from the common potential (obtained at the shield in paddle 28) to charge and discharge control circuit 161 via conductors 83A, 150A. In response, charge and discharge control circuit 161 supplies an output signal on lead 161D to the coil 165A of transfer relay 165, thereby moving the movable contacts thereof from their normal position illustrated in FIG. 11 to a position in contact with the first and second stationary contacts thereof connected to leads 29A',29B'. Previous to this time, the plate electrodes 82,153 will have been brought into contact with the patient. Accordingly, a circuit is completed for the discharge of the energy stored in the capacitor within energy storage circuit 163 through the inductor therein, lead 29A', transfer relay 165, conductor 153A, plate electrode 153, the patient, plate electrode 82, conductor 82A, the transfer relay 165, and lead 29B'.

Concurrently with the provision of an output signal on lead 161D, charge and discharge control circuit 161 removes the steady-state signal from lead 161A to terminate the indication to the user from indicator 86, signifying a discharge. Shortly thereafter, charge and discharge control circuit 161 removes its output signal from the lead 161D, thereby returning the transfer relay to its normal position and concurrently provides a momentary output signal on lead 161C to cause dump relay 162 to apply a bleed resistor across the capacitor in energy storage circuit 163 to terminate the defibrillator pulse (or to discharge the capacitor in the case where the plate electrodes 153,82 are not in contact with a patient). Dump relay 162 is also triggered by charge and discharge control circuit 161 in a case where the user lowers the preselected energy level by manipulation of energy select network 84 before discharge with a signal being provided on lead 161C until the comparator within charge and discharge control circuit 161 again signals that the stored charge equals the preselected energy level.

The aforementioned components of defibrillator 12 largely are conventional and their specific implementation will be apparent to those skilled in the art.

Third and fourth stationary contacts of the transfer relay 165, with which the movable contacts therefor normally engage, are connected via conductors 29A", 29B" to first and second contacts of the slide connector 52, with both conductors 29A", 29B" being shielded, the shield being connected at one point to the defibrillator common potential and at a second point to a third contact of slide connector 52. Surge protectors 167,168 are connected, respectively, from the third and fourth stationary contacts of transfer relay 165 to the defibrillator common potential and provide additional protection of the monitor/recorder 10, when interconnected with defibrillator 12, from overvoltages such as those caused by open-circuit discharges of the defibrillator 12, e.g., those discharges when the plate electrodes 153,82 are not in contact with the patient.

In monitor/recorder 10, first and second contacts of slide connector 44 corresponding to the first and second contacts of slide connector 52 are connected via conductor 177,178 to first and second stationary contacts of the patient cable-paddle switch 23A.

The conductors 177,178 are shielded, with the shield connected at one point to the monitor/recorder common potential and at second point to a third contact of slide connector 44 corresponding to the third contact of slide connector 52.

The three-lead patient cable 170 is shown in FIG. 11 as including three patient terminals and leads LL (left leg), RA (right arm) and LA (left arm), together with a shield therefor which are connected to respective terminals of the patient cable conector 23B. A lead 171 connects that terminal of connector 23B connected to the LL lead of cable 170 to a third stationary terminal of switch 23A, and a lead 172 connects that terminal of connnector 23B connected to lead RA of cable 170 to a fourth stationary terminal of switch 23A. Surge protectors 174 and 175 connected, respectively, from leads 171 and 172 to the monitor/recorder common potential, provide overvoltage protection for the monitor/recorder 10. The LA lead, which is used as a reference for the EKG waveforms on the LL and RA leads, is likewise protected by a surge protector 176 connected by a lead 173 to that terminal of connector 23B connected to a lead LA and to the monitor/recorder common potential. The shield of cable 170 is connected directly to the monitor/recorder common potential through connector 23B.

Movable contacts of switch 23A are connected via conductors 179,180 to first and second signal inputs of a balanced preamplifier stage of a conventional EKG monitor and recorder 181, with conductors 179 and 180 being shielded. The shield is connected at one point to the monitor/recorder common potential and at a second point to a third or reference input of the preamplifier state of EKG monitor and recorder 181.

In the position of switch 23A illustrated in FIG. 11, EKG monitor and recorder 181 is connected to the patient via the patient cable 170. When switch 23A is put into its second position wherein the movable contacts thereof are in contact with the first and second stationary contacts thereof, the EKG monitor and recorder 181 is connected to the patient through leads 177 and 178, slide connector 44, slide connector 52, leads 29A", 29B"B, transfer relay 165, conductors 153A, 82A and plate electrode 153,82. There is no other electrical interconnection between monitor/recorder 10 and defibrillator 12. It should be particularly noted that the EKG monitor and recorder 181 includes its own power supply 182 for receiving power from the battery pack 24.

Thus, it should be apparent to those skilled in the art that the monitor/recorder 10 and defibrillator 12 can operate independently as stand-alone items, or in combination through electrical interconnection via slide connectors 44 and 52 to provide a monitoring through the paddles feature.

Although the invention has been described with respect to a preferred embodiment, it is to be clearly understood by those skilled in the art that the invention is not limited thereto, but rather is intended to be bounded only by the limits of the appended claims.

What is claimed is:

1. An improved electrical connector, for an electronic physiological instrument which is contained within a housing having an exterior housing surface, the housing also having a cut away portion defining a housing aperture connector comprising:
   (a) a central contact support member of insulating material, said central contact support member having a substantially rectangular, substantially planar front surface and a pair of opposite, substantially parallel side surfaces bounding said front surface,
   (b) first and second contact retaining members, each of insulating material, and each having a substantially planar front surface and an adjoining side surface complementary to one of said pair of side surfaces of said central contact support member,
   (c) a plurality of metallic, leaf spring contacts, each of said contacts being formed into a substantial U-shape and thereby having a central, bowed contact portion, and adjoining first and second legs, each of said legs having extending therethrough an aperture, and electrical terminal means being provided on one of said legs,
   (d) a plurality of projections formed and extending from the side surfaces of one of said central contact support member or said first and second contact retaining members, said plurality of projections being spaced from each other, and a corresponding plurality of recesses formed in the side surfaces of the other of said central contact support member or said first and second contact retaining members, said plurality of recesses being spaced apart from each other,
   (e) said first and second contact retaining members being secured to said central contact support member, with each one of said plurality of projections passing through one of said apertures in one of said plurality of contacts and being received in a corresponding one of said plurality of recesses to form a connector assembly, said plurality of projections and said plurality of recesses being located so that said front surfaces of said central contact support member and said first and second contact retaining members are substantially coplanar in said connector assembly; and,
   (f) means adapted to mount said connector assembly in the housing aperture so that said front surfaces of said central contact support member and said first and second contact retaining members are substantially flush with the exterior housing surface.

2. The improved electrical connector as recited in claim 1, wherein said plurality of recesses are provided in said side surfaces of said first and second contact retaining members and wherein said plurality of projections are provided on said side surfaces of said central contact support member.

3. The improved electrical connector as recited in claim 1, wherein said mounting means comprises peripheral tongues formed on and extending from said central contact support member and said first and second contact retaining members for engaging corresponding grooves in the cut away portion of the housing.

4. The improved electrical connector as recited in claim 1, wherein said substantially planar front surfaces of said first and second contact retaining members have respective edge portions adjoining said side surfaces thereof, each said edge portion indented with respect to the remainder of its corresponding front surface and said plurality of projections and said plurality of recesses being located so that said edge portions and said front surface of said central contact support member are substantially coplanar in said connector assembly to form a recess for said plurality of metallic, leaf spring contacts.

* * * * *

UNITED STATES PATENT AND TRADEMARK OFFICE
CERTIFICATE OF CORRECTION

PATENT NO. : 4,097,113
DATED : June 27, 1978
INVENTOR(S) : Stephen L. McKelvy

It is certified that error appears in the above-identified patent and that said Letters Patent are hereby corrected as shown below:

Column 2, line 68: "susceptability" is changed to —susceptibility—.

Column 3, line 29: "extending" is changed to —extend—.

Column 5, line 1: "in" is changed to —is—.

Column 6, line 62: "is" is changed to —in—.

Column 11, line 25: "thorugh" is changed to —through—.

Column 12, line 67: "29B"B " is changed to —29B"—.

Column 12, line 68: "electrode" is changed to —electrodes—.

Column 13, line 22: after "aperture", insert —which extends into the housing from the exterior housing surface, said—.

Column 14, line 38: —being— is inserted after "portion".

Signed and Sealed this

Second Day of January 1979

[SEAL]

Attest:

RUTH C. MASON
Attesting Officer

DONALD W. BANNER
Commissioner of Patents and Trademarks